United States Patent
Fry et al.

(10) Patent No.: US 11,779,386 B2
(45) Date of Patent: Oct. 10, 2023

(54) TWO-PART SEAL PLATE FOR VESSEL SEALER AND METHOD OF MANUFACTURING SAME

(71) Applicant: Covidien LP, Mansfield, MA (US)

(72) Inventors: Monte S. Fry, Longmont, CO (US); Grant T. Sims, Boulder, CO (US); Robert F. Mccullough, Jr., Boulder, CO (US)

(73) Assignee: Covidien LP, Mansfield, MA (US)

( * ) Notice: Subject to any disclaimer, the term of this patent is extended or adjusted under 35 U.S.C. 154(b) by 336 days.

(21) Appl. No.: 16/850,059

(22) Filed: Apr. 16, 2020

(65) Prior Publication Data

US 2021/0322089 A1 Oct. 21, 2021

(51) Int. Cl.
| | | |
|---|---|---|
| A61B 18/12 | (2006.01) | |
| A61B 18/14 | (2006.01) | |
| A61B 17/00 | (2006.01) | |
| B29C 69/00 | (2006.01) | |
| A61B 17/29 | (2006.01) | |
| A61B 18/00 | (2006.01) | |

(52) U.S. Cl.
CPC .............. *A61B 18/1445* (2013.01); *A61B 2017/00526* (2013.01); *A61B 2017/2911* (2013.01); *A61B 2018/0063* (2013.01); *A61B 2018/126* (2013.01); *A61B 2018/1455* (2013.01); *B29C 69/00* (2013.01)

(58) Field of Classification Search
CPC ........ A61B 18/1445; A61B 2018/0063; A61B 2018/126; A61B 2018/1455
See application file for complete search history.

(56) References Cited

U.S. PATENT DOCUMENTS

| | | | |
|---|---|---|---|
| 5,489,292 A | * | 2/1996 | Tovey ................ A61B 17/282 |
| | | | 606/174 |
| 5,542,432 A | * | 8/1996 | Slater ................ A61B 10/0266 |
| | | | 600/564 |
| 7,156,846 B2 | | 1/2007 | Dycus et al. |
| 8,016,827 B2 | | 9/2011 | Chojin |
| 8,197,633 B2 | | 6/2012 | Guerra |
| 8,226,650 B2 | | 7/2012 | Kerr |
| 8,292,886 B2 | | 10/2012 | Kerr et al. |
| 8,333,765 B2 | | 12/2012 | Johnson et al. |
| 8,382,792 B2 | | 2/2013 | Chojin |
| 8,469,957 B2 | | 6/2013 | Roy |
| 8,535,312 B2 | | 9/2013 | Horner |
| 8,568,412 B2 | | 10/2013 | Brandt et al. |
| 8,623,018 B2 | * | 1/2014 | Horner ............... A61B 18/1442 |
| | | | 606/51 |
| 8,632,564 B2 | | 1/2014 | Cunningham |
| 8,740,901 B2 | | 6/2014 | Johnson et al. |
| 8,968,308 B2 | | 3/2015 | Horner et al. |

(Continued)

*Primary Examiner* — Daniel W Fowler
(74) *Attorney, Agent, or Firm* — Carter, DeLuca & Farrell LLP

(57) ABSTRACT

A method of manufacturing a two-part sealing plate of a jaw member of an end effector assembly includes: fabricating a series of grooves through an upper plate of a two-part sealing plate of a jaw member; securing a lower plate to a non-tissue engaging side of the upper plate such that an upper surface of the lower plate defines a corresponding bottom surface of at least one of the series of grooves; and securing the seal plate to a support base of the jaw member.

20 Claims, 8 Drawing Sheets

(56) References Cited

U.S. PATENT DOCUMENTS

| | | |
|---|---|---|
| 8,968,312 B2 | 3/2015 | Marczyk et al. |
| 8,968,314 B2 | 3/2015 | Allen, IV |
| 9,113,882 B2 | 8/2015 | Twomey et al. |
| 9,113,889 B2 | 8/2015 | Reschke |
| 9,113,941 B2 | 8/2015 | Kappus et al. |
| 9,161,806 B2 | 10/2015 | Brandt et al. |
| 9,265,552 B2 | 2/2016 | Brandt et al. |
| 9,265,565 B2 | 2/2016 | Kerr |
| 9,265,569 B2 | 2/2016 | Hart et al. |
| 2003/0229344 A1 | 12/2003 | Dycus et al. |
| 2004/0181214 A1* | 9/2004 | Garabedian ........ A61B 18/1477 606/41 |
| 2005/0159778 A1* | 7/2005 | Heinrich ............ A61B 18/1445 606/216 |
| 2007/0074807 A1* | 4/2007 | Guerra ................ B29C 70/72 156/242 |
| 2009/0012520 A1* | 1/2009 | Hixson .............. A61B 18/1445 606/51 |
| 2009/0182331 A1* | 7/2009 | D'Amelio et al. ........................ A61B 18/1442 606/51 |
| 2009/0248021 A1 | 10/2009 | McKenna |
| 2009/0254081 A1 | 10/2009 | Allison et al. |
| 2009/0292282 A9 | 11/2009 | Dycus |
| 2010/0063500 A1 | 3/2010 | Muszala |
| 2011/0073246 A1* | 3/2011 | Brandt ............... A61B 18/1445 156/379 |
| 2012/0215215 A1* | 8/2012 | Reschke ............ A61B 18/1445 606/37 |
| 2012/0239034 A1 | 9/2012 | Horner et al. |
| 2012/0271346 A1* | 10/2012 | Townsend ......... A61B 18/1445 606/205 |
| 2013/0079774 A1 | 3/2013 | Whitney et al. |
| 2013/0232753 A1* | 9/2013 | Ackley ............. A61B 18/1442 29/407.05 |
| 2013/0238017 A1 | 9/2013 | Kerr et al. |
| 2013/0267948 A1 | 10/2013 | Kerr et al. |
| 2014/0243824 A1 | 8/2014 | Gilbert |
| 2015/0018824 A1 | 1/2015 | Allen, IV et al. |
| 2015/0223861 A1 | 8/2015 | Brandt et al. |
| 2015/0327907 A1* | 11/2015 | Stringham ............ C23C 30/005 606/29 |
| 2016/0030105 A1* | 2/2016 | Mayer .................... B22F 10/47 219/121.66 |
| 2016/0157923 A1* | 6/2016 | Ding .................. A61B 17/2812 606/51 |
| 2016/0199125 A1* | 7/2016 | Jones ................ A61B 18/1445 606/49 |
| 2016/0235473 A1* | 8/2016 | Hagland ............ A61B 18/1442 |
| 2017/0238991 A1* | 8/2017 | Worrell ................ H05K 3/0011 |
| 2017/0312017 A1* | 11/2017 | Trees ................ A61B 18/1445 |
| 2019/0328450 A1 | 10/2019 | Sartor et al. |
| 2020/0000515 A1 | 1/2020 | Garrison |
| 2020/0038098 A1 | 2/2020 | Sartor et al. |
| 2020/0060753 A1 | 2/2020 | Joseph |

\* cited by examiner

TWO-PART SEAL PLATE FOR VESSEL SEALER AND METHOD OF MANUFACTURING SAME

BACKGROUND

Technical Field

The present disclosure relates to an apparatus for performing an electrosurgical procedure. More particularly, the present disclosure relates to an apparatus for performing an electrosurgical procedure and a method of manufacturing the same that employs an end effector assembly including a two-part sealing plate to enhance gripping and sealing tissue.

Background of the Related Art

Electrosurgical apparatuses (e.g., electrosurgical forceps) are well known in the medical arts and typically include a handle, a shaft and an end effector assembly operatively coupled to a distal end of the shaft that is configured to manipulate tissue (e.g., grasp and seal tissue). Electrosurgical forceps utilize both mechanical clamping action and electrical energy to effect homeostasis by heating the tissue and blood vessels to coagulate, cauterize, fuse, seal, cut, desiccate, and/or fulgurate tissue.

Electrosurgical forceps may be so-called open forceps for use when accessing open body cavities or open surgical access points, e.g., incisions, or so-called endoscopic forceps for remotely accessing organs through smaller, puncture-like incisions. With endoscopic surgeries, patients tend to benefit from less scarring, less pain, and reduced healing time. The endoscopic forceps is inserted into the patient through one or more various types of cannulas or access ports (typically having an opening that ranges from about five millimeters to about fifteen millimeters) that has been made with a trocar.

Open and endoscopic forceps both utilize an end effector assembly disposed at a distal end thereof for treating tissue between a pair of opposing jaw members. Each jaw member includes an electrically conductive surface or sealing plate used to treat or seal tissue grasped therebetween. Typically, one or both sealing plates includes a series of grooves or indentations disposed thereon configured to enhance gripping tissue during the sealing process.

SUMMARY

In accordance with aspects of the present disclosure, a jaw member for an end effector assembly includes a support base and an electrical jaw lead adapted to operably connect to an electrosurgical generator. A sealing plate is operably coupled to the support base and includes: an upper plate having an outer peripheral edge that depends therefrom and that defines a cavity configured to receive a lower plate; and a series of grooves defined within the upper plate and projecting therethrough to expose the lower plate. One or both of the upper plate or the lower plate is operably coupled to the electrical lead.

In aspects according the present disclosure, the lower plate is made from an electrically conductive material, electrically non-conductive material, thermally conductive material and/or thermally non-conductive material or combinations thereof.

In aspects according the present disclosure, the upper plate includes a knife slot defined therethrough configured to reciprocate a knife therealong upon actuation thereof. In other aspects according the present disclosure, the lower plate includes a knife slot defined at least partially therethrough aligned in vertical registration with the knife slot defined within the upper plate.

In aspects according the present disclosure, the lower plate extends at least partially along the length of the upper plate. In yet other aspects according the present disclosure, the outer peripheral edge of the upper plate is configured to mechanically engage the support base. In still other aspects according the present disclosure, an upper surface of the lower plate defines a corresponding bottom surface of at least one of the plurality of grooves.

Aspects of the present disclosure also relate to a method of manufacturing a two-part sealing plate of a jaw member of an end effector assembly and includes the steps of: fabricating a series of grooves through an upper plate of a two-part sealing plate of a jaw member; securing a lower plate to a non-tissue engaging side of the upper plate such that an upper surface of the lower plate defines a corresponding bottom surface of at least one of the plurality of grooves; and securing the seal plate to a support base of the jaw member.

In aspects according the present disclosure, the lower plate is secured to the non-tissue engaging side of the upper plate via laser welding, mechanical interfacing surfaces and/or gluing. The lower plate may also be trapped during an overmolding process. In addition, the lower plate can be molded into a first shot overmold then the underside of the top plate can be mated and/or connected to a subassembly with a second overmold.

In other aspects according the present disclosure, the method further includes fabricating a knife slot within the upper plate configured to reciprocate a knife therealong upon actuation thereof. In still other aspects according the present disclosure, the method further includes fabricating a knife slot within at least a portion of the lower plate in vertical registration with the knife slot of the upper plate.

In aspects according the present disclosure, the method further includes bending an outer peripheral edge of the upper plate to define a cavity configured to receive the lower plate.

In aspects according the present disclosure, the method further includes jogging an electrical connection from the upper plate around or through the lower plate and feeding the electrical connection proximally through the jaw member. In other aspects according the present disclosure, the method further includes securing the upper and lower plate to the housing via overmolding. In still other aspects according the present disclosure, the overmolding additionally secures the electrical connection within the jaw member.

Aspects of the present disclosure also relate to a method of manufacturing a two-part sealing plate of a jaw member of an end effector assembly and includes: fabricating a series of grooves through an upper plate of a two-part sealing plate of a jaw member; securing a lower plate to a non-tissue engaging side of the upper plate such that an upper surface of the lower plate defines a corresponding bottom surface of at least one of the series of grooves and an extension portion of the lower plate extends proximally beyond the proximal end of the upper seal plate. The extension portion is raised relative to the lower plate and extending beyond the plane of the upper plate, the extension portion acting as a stop member to control the distance between the jaw member and an opposing jaw member of the end effector assembly. This method further includes securing the seal plate to a support base of the jaw member.

In aspects according the present disclosure, the lower plate is secured to the non-tissue engaging side of the upper plate via at least one of laser welding, resistance welding, percussive arc welding, mechanical interfacing surfaces or adhesive.

In aspects according the present disclosure, the method further includes fabricating a knife slot within the upper plate configured to reciprocate a knife therealong upon actuation thereof. In other aspects according the present disclosure, the method further includes fabricating a knife slot within at least a portion of the lower plate in substantial vertical registration with the knife slot of the upper plate.

Aspects of the present disclosure also relate to a method of manufacturing a two-part sealing plate of a jaw member of an end effector assembly and includes: fabricating a series of grooves through an upper plate of a two-part sealing plate of a jaw member; securing a lower plate to a non-tissue engaging side of the upper plate such that an upper surface of the lower plate defines a corresponding bottom surface of at least one of the series of grooves and an extension portion of the lower plate extends proximally beyond the proximal end of the upper seal plate, the extension portion being raised relative to the lower plate and extending beyond the plane of the upper plate. The extension portion acts as a tissue stop to control the ingress of tissue between the jaw member and an opposing jaw member of the end effector assembly when sealing. The method further includes securing the seal plate to a support base of the jaw member.

In aspects according the present disclosure, the lower plate is secured to the non-tissue engaging side of the upper plate via at least one of laser welding, resistance welding, percussive arc welding, mechanical interfacing surfaces or adhesive.

In aspects according the present disclosure, the method further includes fabricating a knife slot within the upper plate configured to reciprocate a knife therealong upon actuation thereof. In other aspects according the present disclosure, the method further includes fabricating a knife slot within at least a portion of the lower plate in substantial vertical registration with the knife slot of the upper plate.

Aspects of the present disclosure also relate to a method of manufacturing a two-part sealing plate of a jaw member of an end effector assembly, including the steps of: forming a progressive strip including an upper plate and a lower plate connected via a web; fabricating a series of grooves through the upper plate; folding the lower plate relative to the upper plate in dimensional alignment therewith; securing the lower plate to a non-tissue engaging side of the upper plate such that an upper surface of the lower plate defines a corresponding bottom surface of one or more of the plurality of grooves; removing the web; and securing the upper plate to a support base of the jaw member.

In aspects according the present disclosure, the method further includes fabricating a knife slot within the upper plate configured to reciprocate a knife therealong upon actuation thereof. In aspects according the present disclosure, the method further includes fabricating a knife slot within at least a portion of the lower plate in substantial vertical registration with the knife slot of the upper plate. In other aspects according the present disclosure, the method further includes bending an outer peripheral edge of the upper plate to define a cavity configured to receive the lower plate.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
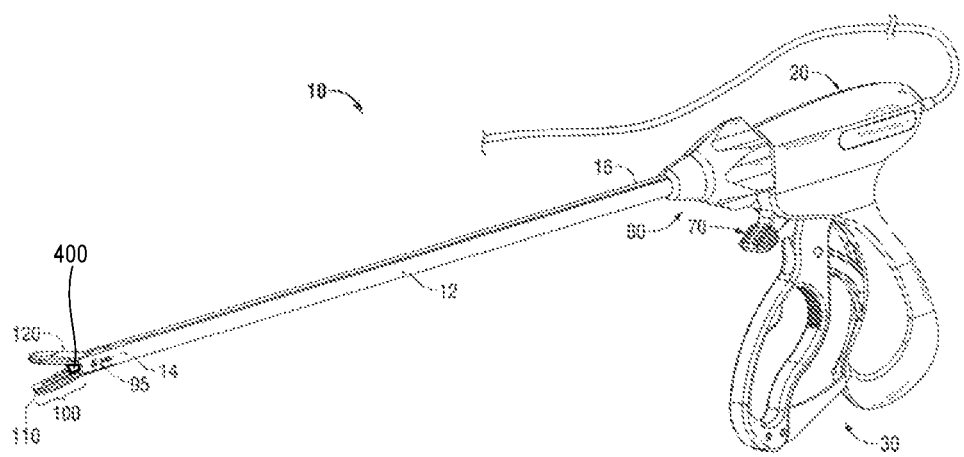
FIG. 1 is a perspective view of an endoscopic bipolar forceps in accordance with an embodiment of the present disclosure.

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus which is closer to the user and the term "distal" refers to the end of the apparatus which is farther away from the user. The term "clinician" refers to any medical professional (i.e., doctor, surgeon, nurse, or the like) performing a medical procedure involving the use of embodiments described herein.

As used herein, the term "fabricating" refers generally to the process of making holes through the seal plates to other material. It is intended to include any process that may be used to make holes through the seal plates or other material including, but not limited to, etching, blanking, EDM-ing, molding, or any other technique known in the art.

Turning now to FIG. 1, an instrument generally identified as forceps 10 may be used during various surgical procedures and includes a housing 20, a handle assembly 30, a rotating assembly 80, a trigger assembly 70, and an end effector assembly 100 that mutually cooperate to grasp, seal, and divide tubular vessels and vascular tissues. Forceps 10 includes a shaft 12 that has a distal end 14 dimensioned to mechanically engage the end effector assembly 100 and a proximal end 16 that mechanically engages the housing 20. The end effector assembly 100 includes opposing jaw members 110 and 120, which cooperate to effectively grasp tissue for sealing purposes. The jaw members 110 and 120 may be curved to facilitate manipulation of tissue and to provide better "line of sight" for accessing targeted tissues.

Examples of forceps are shown and described in commonly-owned U.S. application Ser. No. 10/369,894 entitled "VESSEL SEALER AND DIVIDER AND METHOD MANUFACTURING SAME" and commonly owned U.S. application Ser. No. 10/460,926 (now U.S. Pat. No. 7,156, 846) entitled "VESSEL SEALER AND DIVIDER FOR USE WITH SMALL TROCARS AND CANNULAS.

Figure 2:
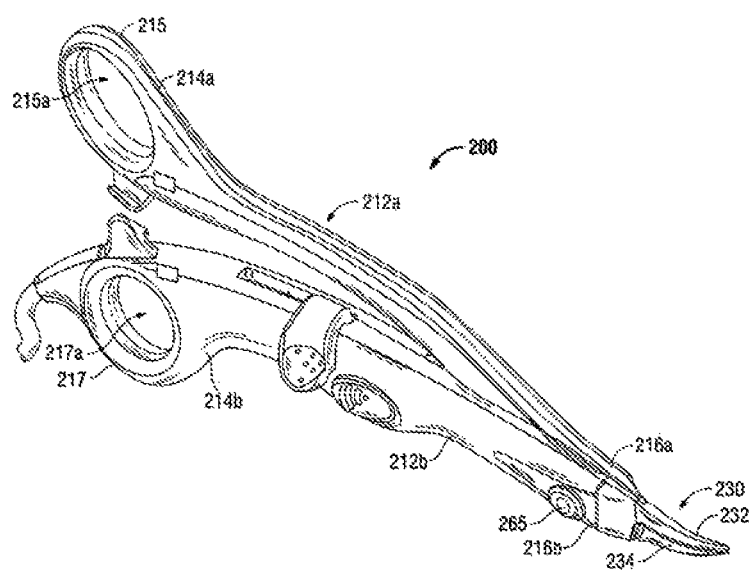
FIG. 2 is a perspective view of an open bipolar forceps in accordance with an embodiment of the present disclosure.
Figure 3A:
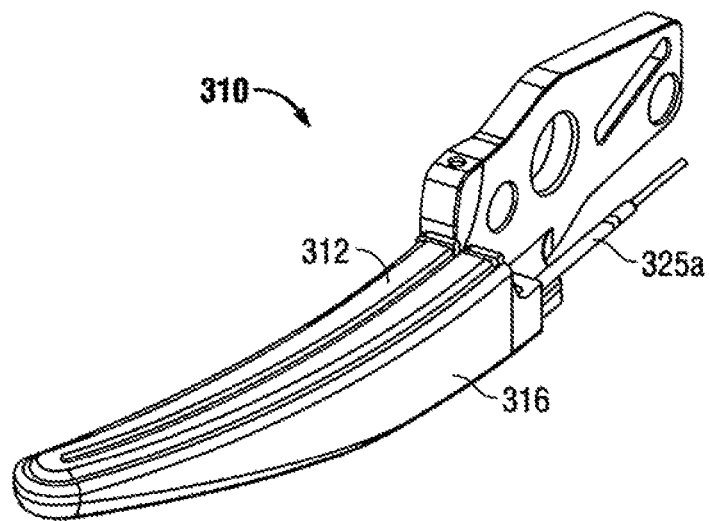
FIGS. 3A and 3B are perspective views of opposing jaw members according to an embodiment of the present disclosure.
Figure 3B:
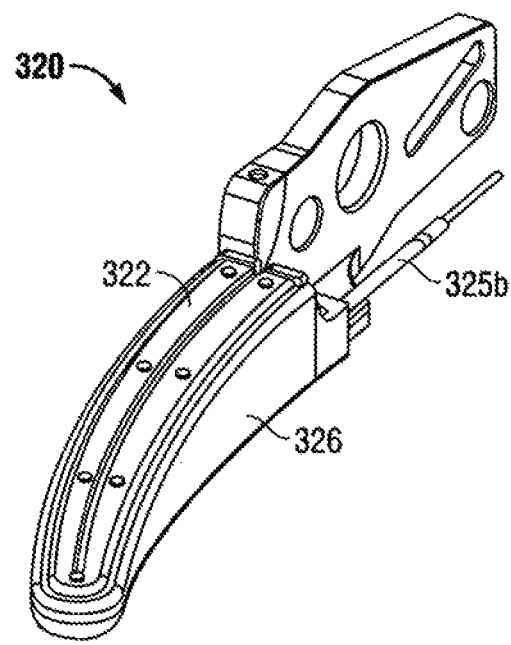

With regard to FIG. 2, an open forceps 200 for use with various surgical procedures is shown. Forceps 200 includes a pair of opposing shafts 212*a* and 212*b* having an end effector assembly 230 attached to the distal ends 216*a* and 216*b* thereof, respectively. End effector assembly 230 is similar in design to end effector assembly 100 and includes pair of opposing jaw members 232 and 234 that are pivotably connected about a pivot pin 265 and that are movable relative to one another to grasp tissue. Each shaft 212*a* and 212*b* includes a handle 215 and 217, respectively, disposed at the proximal end 214*a* and 214*b* thereof. Each handle 215 and 217 defines a finger hole 215*a* and 217*a*, respectively, therethrough for receiving a finger of the user. Finger holes 215*a* and 217*a* facilitate movement of the shafts 212*a* and 212*b* relative to one another which, in turn, pivot the jaw members 232 and 234 from an open position wherein the jaw members 232 and 234 are disposed in spaced relation relative to one another to a clamping or closed position wherein the jaw members 232 and 234 cooperate to grasp tissue therebetween.

FIGS. 3A-4B are perspective views of opposing jaw members 310 and 320. Similar to jaw members 110 and 120, each of the jaw members 310 and 320 include: sealing plates 305 and 335, respectively; electrical jaw leads 325*a* and 325*b*, respectively; and support bases 316 and 326 formed as plastic overmolds. Electrical jaw leads 325*a* and 325*b* supply energy to one or both of the opposing jaw members 310 and 320. Each sealing plate 305, 335 includes an upper sealing plate 312, 322 and a lower sealing plate 311, 337, respectively (See FIG. 4B).

Figure 4A:
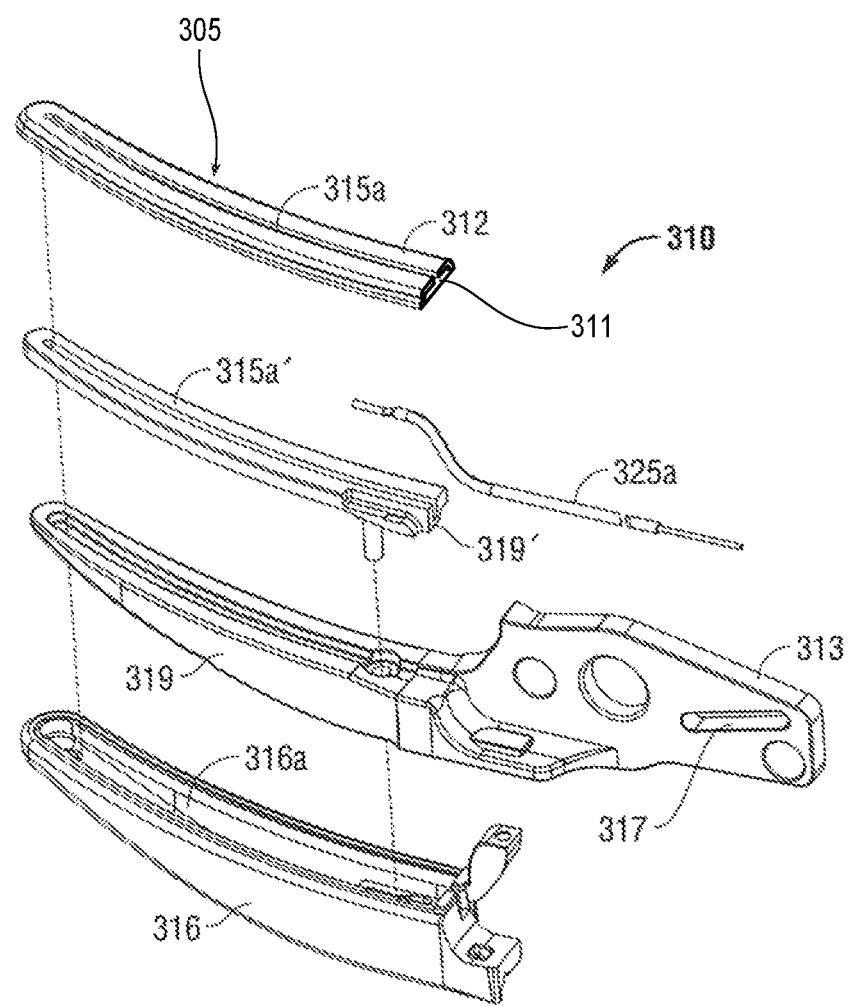
FIGS. 4A and 4B are exploded views of the opposing jaw members of FIGS. 3A and 3B respectively.
Figure 4B:
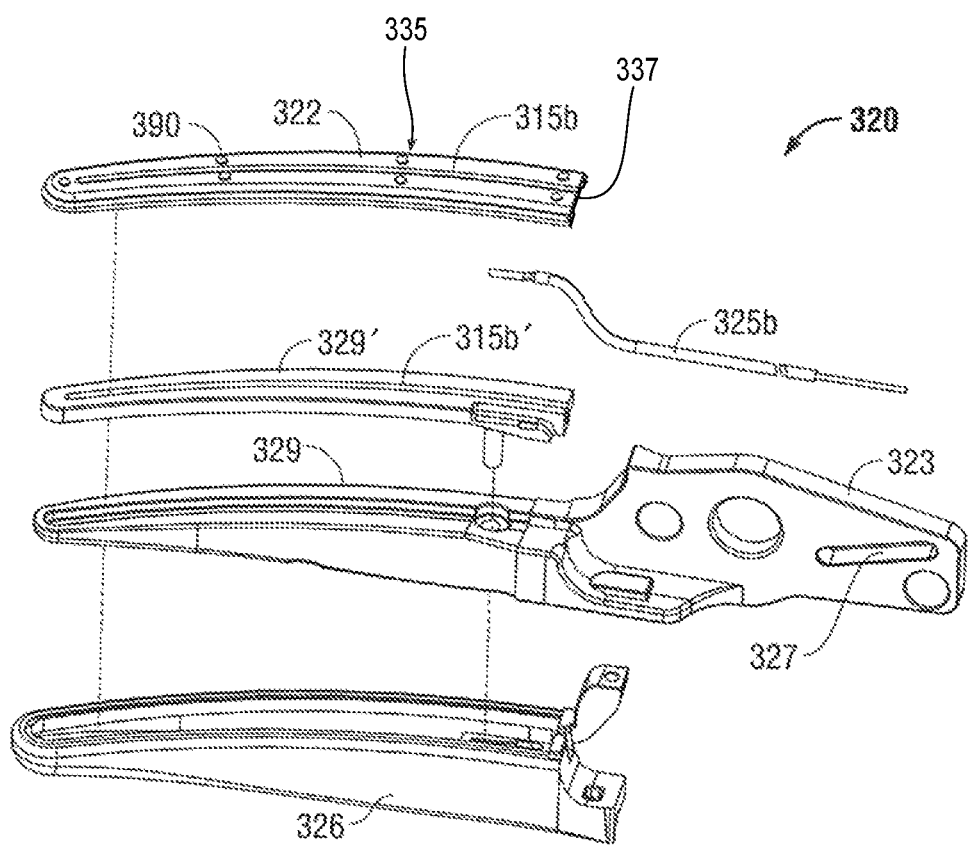

Turning to FIGS. 4A and 4B, the opposing jaw members 310 and 320 include outer housings 316 and 326 and support bases 319 and 329 that extend distally from flanges 313 and 323, respectively. The support bases 316 and 326 are dimensioned to support insulative plates 319' and 329', which in turn, support electrically conductive sealing plates 305 and 335 thereon. Sealing plates 305 and 335 may be affixed atop the insulative plates 319' and 329', respectively, and support bases 319 and 329, respectively, in any known manner in the art, snap-fit, over-molding, stamping, ultrasonically welded, etc. The support bases 319 and 329, insulative plates 319' and 329', and sealing plates 305 and 335 are encapsulated by the outer insulative support bases 316 and 326 by way of a subsequent overmolding process. The jaw members 310 and 320 are connected via an ultrasonic weld, crimping, resistance welding, percussive arc welding, etc. to electrical jaw leads 325*a* and 325*b*, respectively.

As mentioned above, the jaw members 310 and 320 also include proximal flanges 313 and 323 extending proximally from the support bases 319 and 329, respectively, each of which includes an elongated angled cam slot 317 and 327, respectively, defined therethrough. Jaw member 320 includes a series of stop members 390 disposed on the inner facing surface of an upper electrically conductive plate 312 of sealing plate 305 to define a gap between opposing jaw members 310 and 320 during sealing and cutting of tissue. The series of stop members 390 are applied onto the upper plate 312 during manufacturing. Upper plate 312 of sealing plate 305 and upper plate 322 of sealing plate 335 and, in some cases, the insulator plates 319', 329' include respective longitudinally-oriented knife slots 315*a*, 315*a'* and 315*b*, 315*b'*, respectively, defined therethrough for reciprocation of the knife blade 400. In embodiments, only the upper plates 312, 322 include the knife slots 315*a*, 315*a'* and 315*b*, 315*b'*. In other embodiments, the upper plates 312, 322 and the lower plates 311, 337 include the knife slots 315*a*, 315*a'* and 315*b*, 315*b'* defined therethrough.

In various embodiments, the upper plates 312, 322 may be configured to control the movement or path of the knife 400, the lower plates 311, 337 may be configured to control the movement or path of the knife 400, the upper plates 312, 322 and lower plates 311, 337 may work in unison to control the movement or path of the knife, or the upper plates 312, 322 and lower plates 311, 337 may be offset to control the movement or path of the knife 400 (especially when the knife 400 is traveling about a curve).

Figure 5:
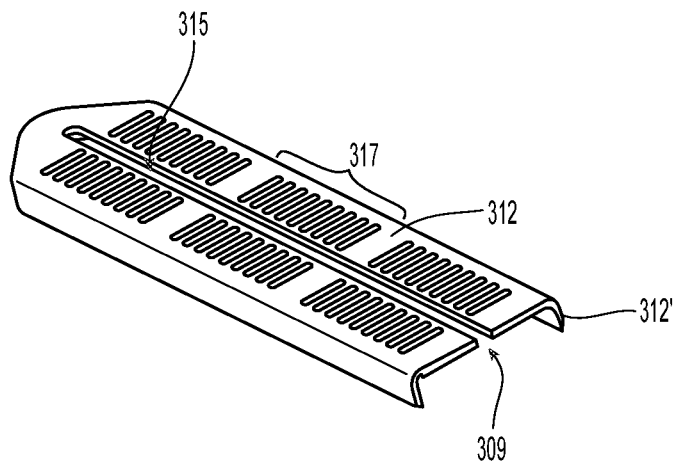
FIG. 5 is an enlarged, rear perspective view of an upper plate of a two-part seal plate according to the present disclosure.
Figure 6:
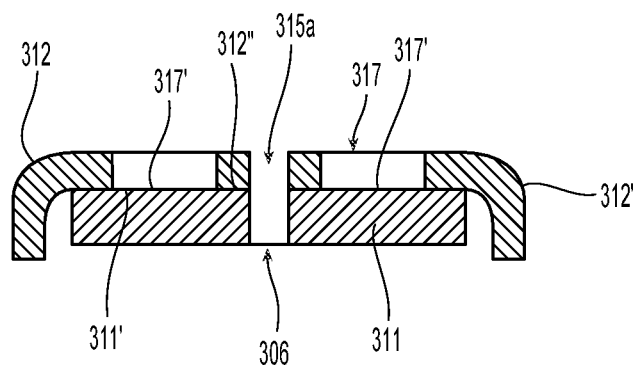
FIG. 6 is an enlarged, cross-sectional view of the two-part seal plate of FIG. 5 showing both the upper plate and a lower plate in accordance with present disclosure.

With reference to FIGS. 5 and 6, a perspective view of the upper plate 312 of sealing plate 305 is shown. For the purposes herein, sealing plate 305 is described, however, sealing plate 335 may be of similar construction. Upper plate 312 includes a series of grooves 317 etched or otherwise formed therethrough configured to facilitate grasping tissue. Knife channel 315*a* is defined through upper plate 312. Flanges 312' depend from the outer peripheral edge of plate 312 and are configured to define a cavity 309 therebetween. Cavity 309 is configured to receive the lower plate 311 (See FIG. 6). Lower plate 311 may be attached to upper plate 312 via laser welding, ultrasonic welding, resistance welding, percussive arc welding, mechanical interlocking surfaces, adhesive or any known method in the art. The upper and lower plates 312, 311 may be aligned and secured to one another without the necessity of the formation of cavity 309.

Fabricating retention features or grooves 317 clean through upper plate 312 and securing the lower plate 311 to form the two-part seal plate 305 provides clean, sharp gripping surfaces compared to traditional methods of creating gripping elements (e.g., grooves) in seal plates.

For example, the two-part seal plate 305 essentially eliminates coining that may occur when partially creating grooves in traditional seal plates. Moreover, creating "blind" texture features (e.g., grooves) in a stamping process adds significant internal stress to the seal plate that can lead to seal plate warping. Still further, for a traditional stamping process to achieve similar effectiveness to even adequately "grip" tissue (and tissue structures), a thicker seal-plate must be used to achieve the appropriate depth of texture to adequately grip tissue as there are limits to the percentage of the thickness of the seal plate that can be coined in a traditional stamping process. Moreover, coining texture onto seal plates also tends to round the top edges of the coined grooves which reduces the effectiveness of the actual "grip" of a seal-plate.

It is envisioned that the lower plate 311 may simply be positioned relative to the upper plate 312 and then secured in some fashion, e.g. overmolded, by a later step.

The disclosed two-part seal plate 305 allows features to be blanked or punched clean through the upper plate 312 of the seal plate 305 and the lower portion of the grooves 317 become supported by the lower plate 311. The depth of the grooves 317 becomes the thickness of the upper plate 312 and is not subject to any coining constraints.

This method of creating the seal plate 305 allows deep, sharp, and clean cuts through the upper plate 312 to maximize gripping versus etching or stamping surfaces. Moreover, the grooves 317 may be cut in a progressive laser cutting process, punching, chemical etching, or the like. Additionally, the direction of the cut may be selected to achieve a desired gripping edge for the grooves 317, e.g., cut from inside-out or outside-in. Sharpness of the gripping edges of the grooves 317 may be managed utilizing one or more secondary processes, e.g., electro-polishing, bead blasting, pickling, or tumbling.

Outer peripheral flange or "skirt" 312' may include one or more mechanical interfaces to enhance securing the seal plate 312 to the support base 319 or outer housing 316 during the attachment process, e.g., overmolding the seal plate 312 to the outer housing 316 via pinch trim, dove tail, etc. Other known methods of mechanical attachment are also contemplated. Utilizing a thinner material for the upper plate 312 facilitates forming the outer peripheral flange 312' as there is less distortion in the forming operation which results in final geometry that is more "CAD representative". This helps with seal plate flatness, over-mold shutoffs, and ultimately better gap control in the forceps 10.

Manufacture of a two part seal-plate 305 allows for additional clearance in critical areas as the lower plate 311 can be relieved in critical areas to increase space between conductive components to ultimately improve dielectric robustness between a jaw member 310 structure and the seal plate 305, e.g., upper plate 312. Moreover, a distal portion of the lower plate 311 may be eliminated to thin the overall seal plate 305 thickness near a distal tip thereof to facilitate finer dissection capabilities.

Figure 7A:
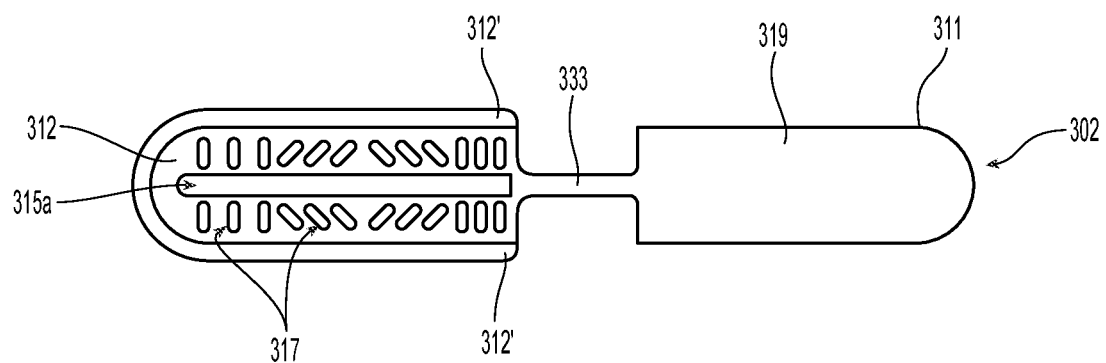
FIG. 7A is an enlarged, top view of the upper and lower plates of the two-part seal plate manufactured in a single piece progressive strip.

The two parts of the seal plate, namely, upper plate 312 and lower plate 311, may be manufactured as a single piece in a progressive stamping or laser cutting process (See FIG. 7A). A webbing 333 may transition the upper plate 312 and the lower plate 311. The webbing 333 may be folded, the two plates laser welded and then de-webbed in a series of in-die or post-op processes. Upon folding, the upper and lower plates 312, 311 may be aligned in dimensional alignment (length and width) relative to one another. In embodiments, the width of the lower plate 311 may be slightly smaller than the width of the cavity 309 such that the lower plate 311 fits therein.

The present disclosure also relates to a method of forming a two-part seal plate 305 of a jaw member 310 and includes the steps of: fabricating a series of grooves 317 through an upper plate 312 of a two-part sealing plate 305 of a jaw member 310; securing a lower plate 311 to a non-tissue engaging side 312" of the upper plate 312 such that an upper surface 311' of the lower plate 311 defines a corresponding bottom surface 317' of at least one of the plurality of grooves 317; and securing the seal plate 305 to a support base 316 of the jaw member 310.

In aspects according the present disclosure, the lower plate 311 is secured to the non-tissue engaging side 312" of the upper plate 312 via laser welding, mechanical interfacing surfaces, resistance welding and/or adhesive. In other aspects according the present disclosure, the method further includes fabricating a knife slot 315a within the upper plate 312 configured to reciprocate a knife 400 (FIG. 1) therealong upon actuation thereof. In still other aspects according the present disclosure, the method further includes fabricating a knife slot 306 within at least a portion of the lower plate 311 in substantial vertical registration with the knife slot 315a of the upper plate. Knife slot 306 may be larger than knife slot 315a depending upon a particular purpose or to facilitate manufacturing and alleviate the need to register the two knife slots 306, 315a during assembly.

In aspects according the present disclosure, the method further includes bending an outer peripheral edge 312' of the upper plate 312 to define a cavity 309 configured to receive the lower plate 311. The outer peripheral surface of the lower plate 311 may be smaller than the inner peripheral surface (e.g., the space between peripheral edges 312') of the upper plate 312 to facilitate manufacturing.

Aspects of the present disclosure also relates to a method of manufacturing a two-part sealing plate 305 of a jaw member 310 and includes the steps of: forming a progressive strip 302 including an upper plate 312 and a lower plate 311 connected via a web(s) 333; fabricating a series of grooves 317 through the upper plate 312; folding the lower plate 311 relative to the upper plate 312 in dimensional alignment therewith; securing the lower plate 311 to a non-tissue engaging side 312" of the upper plate 312 such that an upper surface 311' of the lower plate 311 defines a corresponding bottom surface 317' of one or more of the plurality of grooves 317; removing the web(s) 333; and securing the upper plate 312 to a support base 316 of the jaw member 310.

Figure 7B:
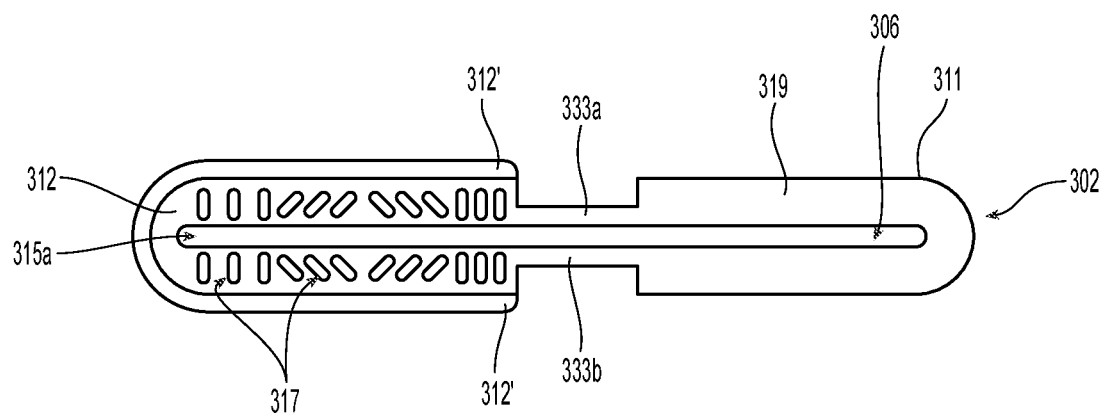
FIG. 7B is an enlarged, top view of the upper and lower plates of another embodiment of the two-part seal plate manufactured in a single piece progressive strip.

FIG. 7B shows two webs 333a, 333b on either side of knife channels 315a, 306. In this instance, both knife channels 315a, 306 may be cut in both plates 312, 311, respectively, during manufacturing. Both webs 333a, 333b are then removed after the plates 312, 311 are folded.

In aspects according the present disclosure, the method further includes fabricating a knife slot 315a within the upper plate 312 (and in some instances, the lower plate 311) configured to reciprocate a knife 400 therealong upon actuation thereof. In aspects according the present disclosure, the method further includes fabricating a knife slot 306 within at least a portion of the lower plate 311 in substantial vertical registration with the knife slot 315a of the upper plate 312. In other aspects according the present disclosure, the method further includes bending an outer peripheral edge 312' of the upper plate 312 to define a cavity 309 configured to receive the lower plate 311.

Figure 8:
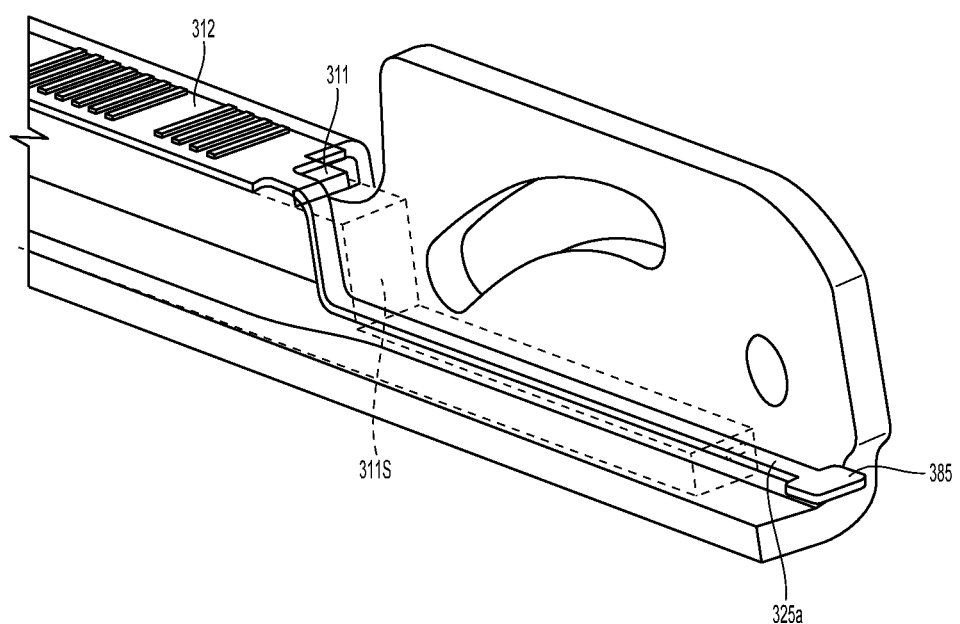
FIG. 8 is an enlarged, rear perspective view of one of the jaw members illustrating a termination tab for electrical connection to the respective seal plate.

It should be understood that the foregoing description is only illustrative of the present disclosure. Various alternatives and modifications can be devised by those skilled in the art without departing from the disclosure. For example, the lower plate 311 may be electrically conductive, thermally conductive, electrically non-conductive or thermally non-conductive or may be a hybrid thereof. Moreover, the present disclosure facilitates feeding the electrical connections (e.g., wire or electrical connection 325a attached to respective upper plate 312) since the electrical connections 325a may be jogged below or around the lower plate 311. Moreover, the electrode connection or wire 325a may be included in the over-mold to the back of the respective seal plates 311, 312. A termination tab 385 may be included to provide ultimate connection to an electrical energy source (FIG. 8).

For example, the lower plate 311 which is electrically conductively coupled to the upper plate may be configured to jog beneath the upper plate 312 in order to facilitate an electrical connection proximally through the respective jaw member 311. It is envisioned that this will maintain full surface area on the upper seal plate 312 for sealing, but enables the lower seal plate 311 to jog the electrical connection/termination underneath the upper seal plate 312 without disrupting the surface area that contacts the tissue.

In embodiments, the lower plate 311 may include a proximal extension 311s that acts as a proximal spacer.

Extension 311s may be utilized to space the jaw members 110, 120 relative to one another or form a gap therebetween to produce an efficient tissue seal. In this instance the extension (or a combination of extensions from the seal plate 312, 322 of respective jaw members 110 and 120) may be raised relative thereto to produce the necessary gap therebetween. In other instances, the proximal extension(s) 311s may be raised and utilized as a tissue stop when tissue is disposed between jaw members 110, 120.

Accordingly, the present disclosure is intended to embrace all such alternatives, modifications and variances. The embodiments described with reference to the attached drawings are presented only to demonstrate certain examples of the disclosure. Other elements, steps, methods and techniques that are insubstantially different from those described above and/or in the appended claims are also intended to be within the scope of the disclosure.

What is claimed is:

1. A method of manufacturing a two-part sealing plate of a jaw member of an end effector assembly, comprising:
    manufacturing an upper plate and a lower plate of a two-part sealing plate for a jaw member as a single piece including the upper plate separated axially from the lower plate by a web interconnecting the upper and lower plates;
    fabricating a series of grooves through the upper plate of the two-part sealing plate of the jaw member, the upper plate formed from an electrically conductive material;
    securing the lower plate of the two-part sealing plate to a non-tissue engaging side of the upper plate such that an upper surface of the lower plate defines a corresponding bottom surface of at least one of the series of grooves, the lower plate formed from an electrically conductive material; and
    securing the two-part sealing plate to a support base of the jaw member.

2. The method of manufacturing a two-part sealing plate of a jaw member of an end effector assembly according to claim 1, wherein the lower plate is secured to the non-tissue engaging side of the upper plate via at least one of laser welding, resistance welding, percussive arc welding, mechanical interfacing surfaces or adhesive.

3. The method of manufacturing a two-part sealing plate of a jaw member of an end effector assembly according to claim 1, further comprising fabricating a knife slot within the upper plate configured to reciprocate a knife therealong upon actuation thereof.

4. The method of manufacturing a two-part sealing plate of a jaw member of an end effector assembly according to claim 3, further comprising fabricating a knife slot within at least a portion of the lower plate in substantial vertical registration with the knife slot of the upper plate.

5. The method of manufacturing a two-part sealing plate of a jaw member of an end effector assembly according to claim 3, further comprising bending an outer peripheral edge of the upper plate to define a cavity configured to receive the lower plate.

6. The method of manufacturing a two-part sealing plate of a jaw member of an end effector assembly according to claim 3, further comprising jogging an electrical connection from the upper plate around the lower plate and feeding the electrical connection proximally through the jaw member.

7. The method of manufacturing a two-part sealing plate of a jaw member of an end effector assembly according to claim 6, further comprising securing the upper and lower plates to an outer housing via overmolding.

8. The method of manufacturing a two-part sealing plate of a jaw member of an end effector assembly according to claim 7, wherein the overmolding additionally secures the electrical connection within the jaw member.

9. The method of manufacturing a two-part sealing plate of a jaw member of an end effector assembly according to claim 2, further comprising securing the upper and lower plates and the support base to an outer housing via overmolding.

10. The method of manufacturing a two-part sealing plate of a jaw member of an end effector assembly according to claim 9, wherein the overmolding additionally secures an electrical connection within the jaw member.

11. The method of manufacturing a two-part sealing plate of a jaw member of an end effector assembly according to claim 1, wherein manufacturing the upper and lower plates further comprises using progressive stamping or laser cutting.

12. The method of manufacturing a two-part sealing plate of a jaw member of an end effector assembly according to claim 1, further comprising folding the web to align the upper plate over the lower plate prior to securing the lower plate to the upper plate.

13. The method of manufacturing a two-part sealing plate of a jaw member of an end effector assembly according to claim 1, wherein the lower plate includes an extension portion and wherein securing the lower plate to the upper plate further comprises extending the extension portion of the lower plate proximally beyond a proximal end of the upper plate, the extension portion being raised relative to the lower plate and extending beyond a plane of the upper plate.

14. A method of manufacturing a two-part sealing plate of a jaw member of an end effector assembly, comprising:
    forming a two-part sealing plate for a jaw member as a single piece made from an electrically conductive material, the two-part sealing plate including an upper plate separated axially from a lower plate by a web interconnecting the upper and lower plates;
    fabricating a series of grooves through the upper plate;
    folding the lower plate into dimensional alignment with the upper plate;
    orienting the lower plate to a non-tissue engaging side of the upper plate such that an upper surface of the lower plate defines a corresponding bottom surface of at least one of the series of grooves; and
    securing the two-part sealing plate to a support base of the jaw member.

15. The method of manufacturing a two-part sealing plate of a jaw member of an end effector assembly according to claim 14, wherein forming the two-part sealing plate includes forming the two-part sealing plate as a progressive strip.

16. The method of manufacturing a two-part sealing plate of a jaw member of an end effector assembly according to claim 14, further comprising welding the upper and lower plates together.

17. The method of manufacturing a two-part sealing plate of a jaw member of an end effector assembly according to claim 16, further comprising removing the web after welding the upper and lower plates together.

18. The method of manufacturing a two-part sealing plate of a jaw member of an end effector assembly according to claim 14, wherein forming the two-part sealing plate further includes forming a knife channel through the upper plate, the web, and the lower plate.

19. The method of manufacturing a two-part sealing plate of a jaw member of an end effector assembly according to claim 14, further comprising bending an outer peripheral edge of the upper plate to define a cavity configured to receive the lower plate.

20. The method of manufacturing a two-part sealing plate of a jaw member of an end effector assembly according to claim 14, further comprising raising an extension portion of the lower plate extending proximally beyond the proximal end of the upper plate beyond a plane of the upper plate.

\* \* \* \* \*